(12) United States Patent
Sieracki et al.

(10) Patent No.: US 8,879,797 B2
(45) Date of Patent: Nov. 4, 2014

(54) SYSTEM AND METHOD FOR TOTAL INTERNAL REFLECTION ENHANCED IMAGING FLOW CYTOMETRY

(75) Inventors: Christian K. Sieracki, Edgecomb, ME (US); Kent A. Peterson, Yarmouth, ME (US); Matthew A. Duplisea, Gorham, ME (US); Corie F. Drake, Portland, ME (US)

(73) Assignee: Fluid Imaging Technologies, Inc., Scarborough, ME (US)

( * ) Notice: Subject to any disclaimer, the term of this patent is extended or adjusted under 35 U.S.C. 154(b) by 135 days.

(21) Appl. No.: 13/480,999

(22) Filed: May 25, 2012

(65) Prior Publication Data

US 2013/0315447 A1 Nov. 28, 2013

(51) Int. Cl.
*G06K 9/00* (2006.01)

(52) U.S. Cl.
USPC ............................................. 382/107

(58) Field of Classification Search
USPC ......... 382/107, 100; 250/458.1, 459.1, 461.2; 356/337, 338, 339, 341, 332, 343
See application file for complete search history.

(56) References Cited

U.S. PATENT DOCUMENTS

| | | | |
|---|---|---|---|
| 3,508,830 A | 4/1970 | Hopkins et al. |
| 4,407,008 A | 9/1983 | Schmidt et al. |
| 4,412,246 A | 10/1983 | Allen et al. |
| 4,612,614 A | 9/1986 | Deindoerfer et al. |
| 5,017,497 A | 5/1991 | de Grooth et al. |
| 5,159,397 A | 10/1992 | Kosaka et al. |
| 5,159,398 A | 10/1992 | Maekawa et al. |
| 5,247,339 A | 9/1993 | Ogino |
| 5,247,340 A | 9/1993 | Ogino |
| 5,248,451 A | 9/1993 | Tsunaga et al. |
| 5,311,290 A | 5/1994 | Olson et al. |
| 5,471,294 A | 11/1995 | Ogino |
| 6,028,663 A | 2/2000 | O'Mongain et al. |
| 6,115,119 A | 9/2000 | Sieracki et al. |
| 7,030,981 B2 | 4/2006 | Bishop et al. |
| 7,599,545 B2 | 10/2009 | Shibata et al. |
| 7,796,256 B2 | 9/2010 | Sieracki et al. |
| 8,005,314 B2 | 8/2011 | Ortyn et al. |
| 2005/0030373 A1 | 2/2005 | Chao et al. |
| 2006/0177937 A1 | 8/2006 | Kurabayashi et al. |
| 2006/0197032 A9 | 9/2006 | Oostman et al. |
| 2007/0139541 A1 | 6/2007 | Fein et al. |
| 2007/0184471 A1 | 8/2007 | Yguerabide et al. |

(Continued)

FOREIGN PATENT DOCUMENTS

JP 2000338030 12/2000

OTHER PUBLICATIONS

Oldenbourg, R., Methods in Molecular Medicine: Analysis of Microtubule Dynamics of Polarized Light, Methods Mol. Med. 2007, 137, 111-123, US.

Johnson, L., Enhanced early detection and enumeration of zebra mussel (*Drieissna* spp.) veligers using cross-polarized light microscopy, Hydrobiologica, 1995, 312, Belgium.

(Continued)

*Primary Examiner* — Yon Couso
(74) *Attorney, Agent, or Firm* — Caseiro Burke LLC; Chris A. Caseiro

(57) ABSTRACT

An imaging flow cytometry system and method which includes a flow chamber, fluorescence analysis and imaging optics, image capturing system, device to regulate fluid flow through the chamber, and backlighting generator. The flow cell is configured so as to enhance the fluorescence signal collection by the system with total internal reflections. The fluorescence collection optics are configured to enhance the collection of the fluorescence from the side of the flow cell and concentrate it on light detectors.

15 Claims, 7 Drawing Sheets

(56) References Cited

U.S. PATENT DOCUMENTS

2009/0273774 A1 11/2009 Sieracki et al.
2009/0283697 A1 11/2009 Sieracki et al.
2010/0027007 A1 2/2010 Adams et al.
2011/0195492 A1 8/2011 Sharpe et al.
2012/0002029 A1 1/2012 Sieracki et al.
2012/0127298 A1 5/2012 Sieracki et al.

OTHER PUBLICATIONS

Marie, D. et al., Enumeration of Marine Viruses in Culture and Natural Samples by Flow Cytometry, Applied and Environmental Microbiology, Jan. 1999, vol. 65, No. 1, 45-52, US.
Statement regarding common ownership of patent documents describing relevant technology, May 25, 2012, 1 pp.
International Search Report and Written Opinion in corresponding PCT application No. PCT/US2013/042285, Nov. 12, 2013, 9 pp.

SYSTEM AND METHOD FOR TOTAL INTERNAL REFLECTION ENHANCED IMAGING FLOW CYTOMETRY

FIELD OF THE INVENTION

The present invention relates generally to an optical flow imaging and analysis configuration used in particle analysis instrumentation, and more particularly to an optical flow imaging system and method incorporating a flow chamber that provides total internal reflections (TIR) of particle fluorescence, enabling more sensitive measurements than previously enabled.

BACKGROUND OF THE INVENTION

Various optical/flow systems employed for transporting a fluid within an analytical instrument to an imaging and optical analysis area exist in the art. A liquid sample is typically delivered into the bore of a flow chamber and the sample is interrogated in some way so as to generate analytical information concerning the nature or properties of the sample. For example, a laser beam may excite the sample present in the bore of the flow cell, and the emitted fluorescence energy provides signal information about the nature of the sample.

If the system is designed to handle a sparse sample with a wide range of particle sizes within it, the flow cell may be rectangular in dimensions and the laser excitation will consist of a fan of laser light rather than a beam of light.

The inefficiencies of standard methods of collecting light from a rectangular flow cell with laser fan illumination can result in weak particle fluorescence which varies greatly with particle position within the flow cell due to the sensitivity of the optics to different optical paths taken by the light on its way to the detector. This poor signal quality is accompanied by high autofluorescence from optical components in existing instruments. Therefore, there is a strong need in the art for an effective way to improve sample fluorescence signal quality and to reduce the background fluorescence level.

SUMMARY OF THE INVENTION

It is an object of the present invention to provide an imaging flow cytometry system and method with improved sample fluorescence signal integrity and strength. It is also an object of the present invention to provide such an improved fluorescence measuring imaging flow cytometer system and method that may be incorporated into, or used with, existing imaging flow cytometers and provide improved fluorescence results. These and other objects are achieved with the present invention, which enables better fluorescence measurements than conventional instruments through introduction of a properly dimensioned flow cell which provides signal gain through internal reflections within the flow cell towards the fluorescence measurement optics. Further, the fluorescence measurement optics are configured with the collection objective perpendicular to the imaging and fluorescence excitation optics and focused on the edge of the flow cell nearest the objective. In other words, the configuration of the flow cell reflects the fluorescence of the sample particles in the channels formed by the water and glass in a manner where light from different particles at different locations in the flow cell reflect with the same efficiency towards the light detectors. In one embodiment, the imaging flow cytometry system and method of the present invention includes a laser fan generator, an imaging and excitation objective, a high aspect ratio rectangular glass flow cell, a high numerical aperture fluorescence emission collecting objective and fluorescence emission analysis optics. The high aspect ratio rectangular glass flow cell allows the fluorescence emissions from the sample to continually reflect back and forth within the sample medium and between the inner sample medium/glass interface and the outer glass/air interface until it emerges from the edge of the flow cell into the fluorescence analysis optics. When this light emerges from the edge of the flow cell, it is coming from a narrow channel which can be efficiently imaged onto the fluorescence analysis optics for signal capture. Specifically, for example, when a properly selected glass flow cell with a sample thickness of 50 to 100 micrometers and a glass wall thickness of 100 micrometers is used with a 0.3 numerical aperture 10× objective, the resulting internal reflection image is only up to 300 micrometers which is easily projected through fluorescence analysis optics with a 3 to 6 millimeter diameter active area. As such, the fluorescence optics are able to collect fluorescence from passing particles efficiently over a large particle position range without focus affecting the signal strength than is otherwise possible. This configuration allows a dramatically improved sample signal collection suitable for analyzing large samples in a short span of time while obtaining accurate fluorescence measurements of particles in the sample. Use of the system and method of the present invention also removes the system autofluorescence observed in conventional imaging flow cytometers such those described in U.S. Pat. No. 6,115,119, incorporated herein by reference, and which uses the same optics for fluorescence excitation and emission measurements. This allows for the use of higher system gain and laser power and hence, much greater sensitivity.

The present invention is a system for imaging particles in a fluid. The system includes a flow chamber, which includes a channel arranged to transport the fluid therethrough at a selectable rate, wherein the flow chamber is configured to enable fluorescence propagation from the fluid within the channel to an edge of the flow chamber for enhanced light collection of the fluorescence, a device configured to create a controllable fluid flow rate in the flow chamber, a backlighting generator arranged to illuminate the fluid in the flow chamber, an objective arranged to receive incident optical radiation from the flow chamber, a light source arranged to generate light scatter and/or fluorescence from particles, one or more detectors to detect light scatter and/or fluorescence emitted from the particles upon illumination, a signal processor configured to receive signals from the one or more detectors and an image capturing system including means to capture images of particles in the fluid. The backlighting generator may be a light emitting diode flash. The backlighting generator generates a high intensity flash. The system also includes a computing device to receive signals from the image capturing system. The image capturing system includes a digital camera or an analog camera and a framegrabber. The image capturing system also includes a CCD or a CMOS camera. The light source may be a laser. The present invention is also an apparatus to assist in the imaging of particles in a fluid, the apparatus comprising a flow chamber including a channel arranged to transport the fluid therethrough at a selectable rate, wherein the flow chamber is configured to enable fluorescence propagation from the fluid within the channel to an edge of the flow chamber for enhanced light collection of the fluorescence.

The present invention also provides a method for imaging particles in a fluid which is transported through a channel of a flow chamber at a selectable rate and illuminated with a light source so that scatter and/or fluorescence signals are detected. The method includes the steps of directing the fluid through the flow chamber, wherein the flow chamber is configured to enable fluorescence propagation from the fluid within the channel to an edge of the flow chamber for enhanced light collection of the fluorescence and imaging the tracked particle and transferring the captured images to a computing device. The method also includes the step of analyzing the image for particles.

The present invention also includes a method for imaging particles in a fluid, which method includes the steps of transporting the fluid through a channel of a flow chamber at a selectable rate, wherein the flow chamber is configured to enable fluorescence propagation from the fluid within the channel to an edge of the flow chamber for enhanced light collection of the fluorescence, illuminating the fluid with a light source arranged to generate light scatter and/or fluorescence from the particles, transmitting a signal from a scatter detector and/or a fluorescence detector to a signal processor and, if the signal meets a predetermined threshold, initiating a particle tracking interval including controlling a tracking mirror, activating a backlighting generator, and activating an image capturing system and imaging the tracked particle and transferring the captured images to a computing device. That method further includes the step of analyzing the image for particles.

These and other advantages of the present invention will become more readily apparent upon review of the following detailed description, the accompanying drawings, and the appended claims.

DETAILED DESCRIPTION OF THE PREFERRED EMBODIMENT

Figure 1:
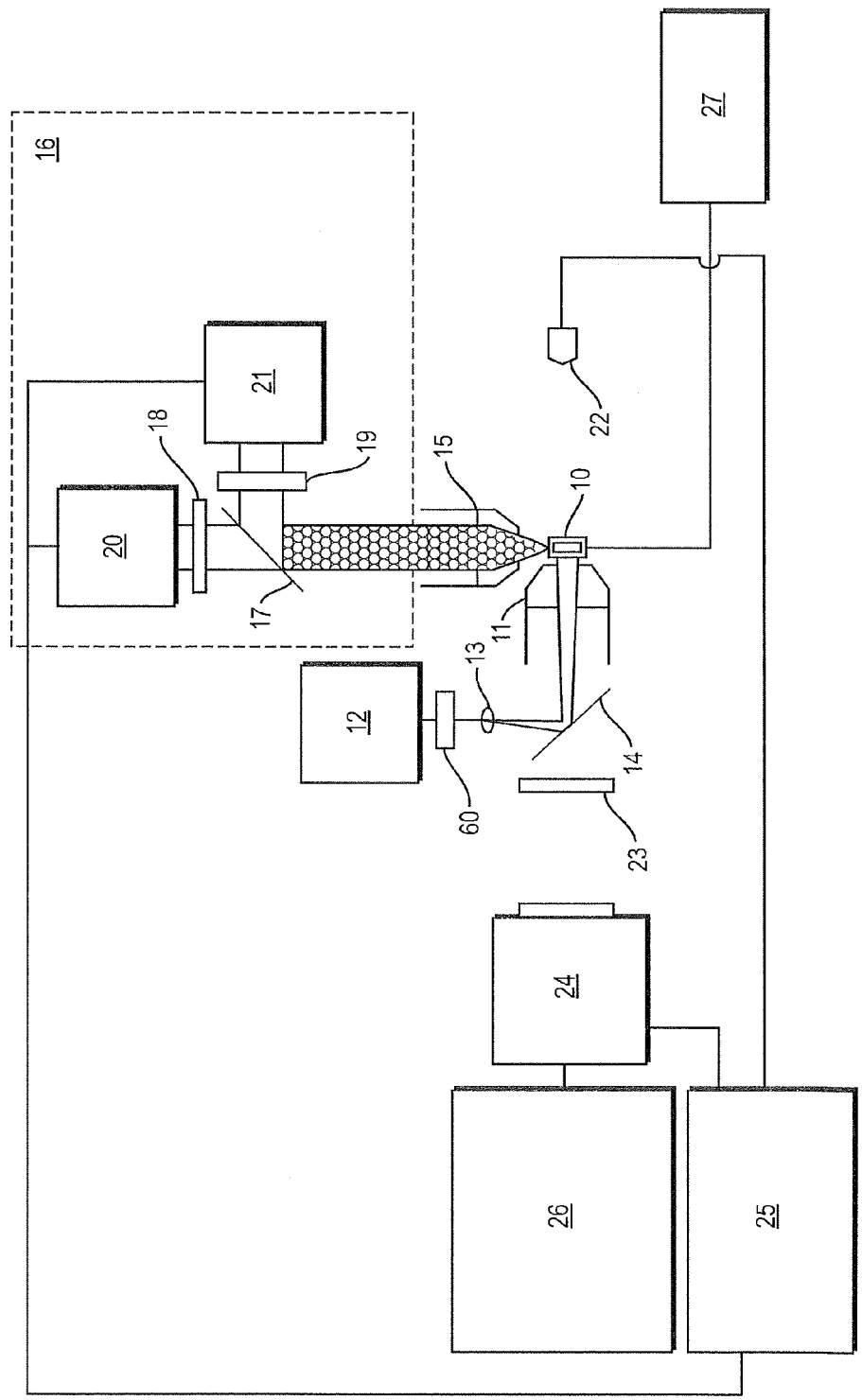
FIG. 1 schematically illustrates a top view of one embodiment of the system of the present invention for analyzing particles in a fluid and FIG. 1A shows a partial cross-sectional side view of the flow chamber with sample source.
Figure 1A:
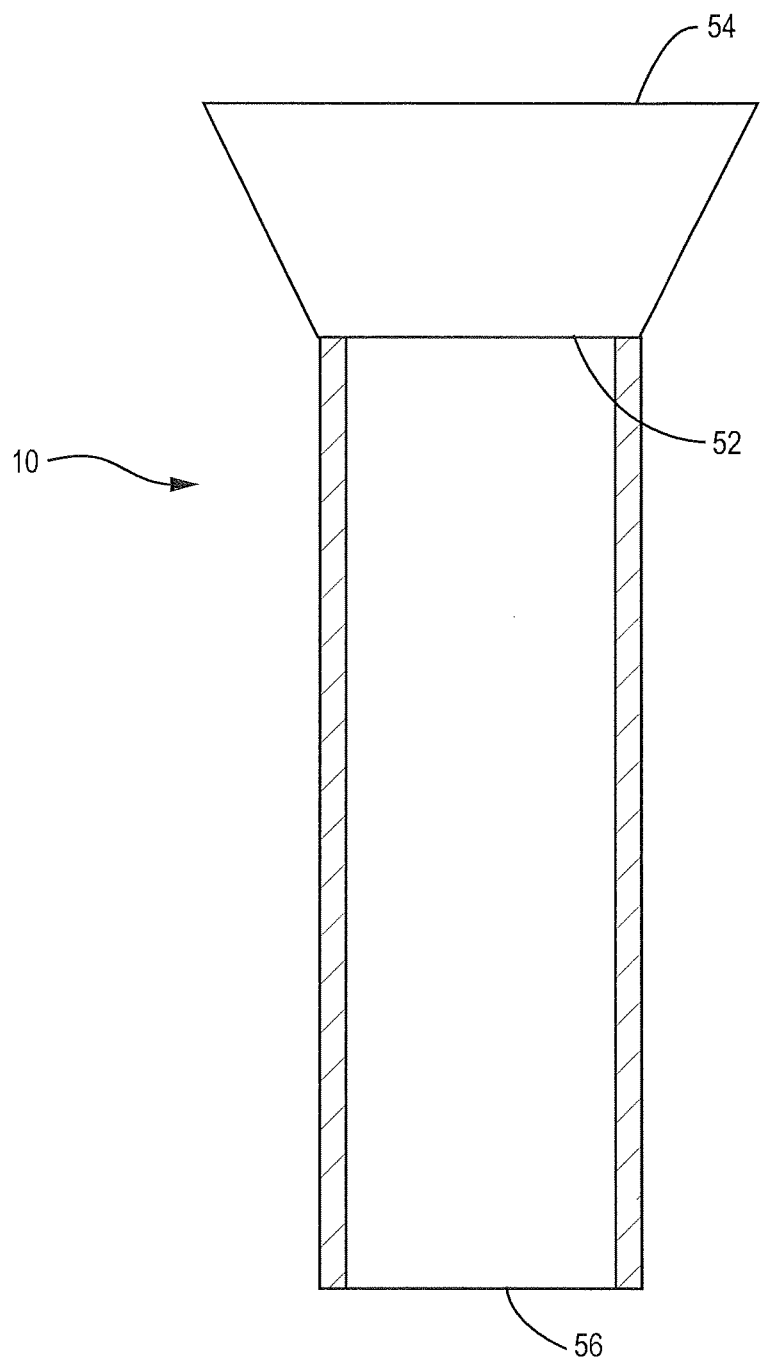

One embodiment of a system of the present invention suitable for high sensitivity automated counting and/or imaging of particles in a fluid is shown in FIG. 1. The system includes a flow chamber 10, which is shown alone in FIG. 1A, an imaging and excitation objective 11, a laser 12, a laser fan generator lens 13, a laser reflecting mirror 14, a fluorescence emission objective 15, fluorescence analysis optics 16, including one or more mirrors represented by longpass dichroic mirror 17, optical filters 18,19 and photomultipliers 20,21, a backlighting source 22, a laser blocking filter 23, an image capturing system 24, a digital signal processor 25, a computing device 26 and a pump 27 capable of delivering a controllable fluid flow rate. The embodiment of the system 10 depicted in FIG. 1 may also include other imaging and analysis in other possible configurations.

Figure 2:
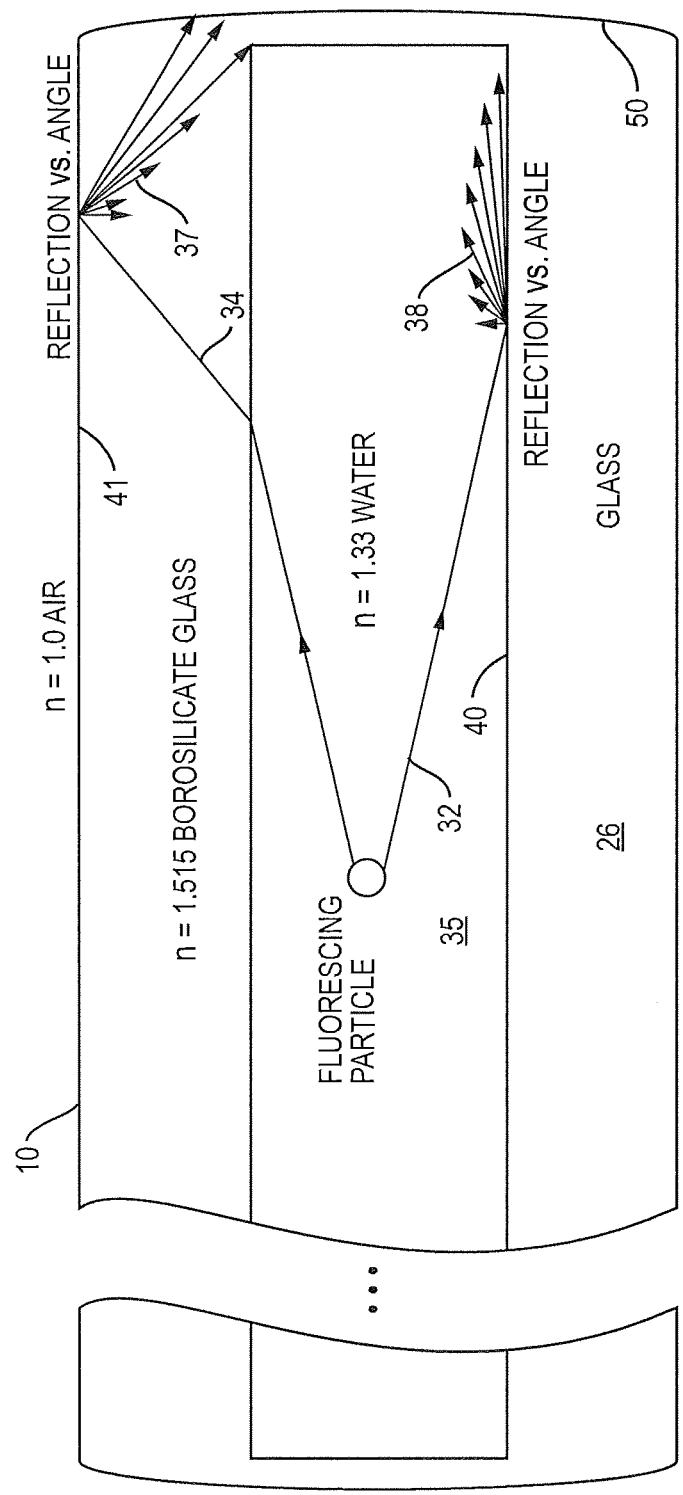
FIG. 2 is a top view of the flow chamber looking down into the channel of the flow chamber with material selected for use in one embodiment of the invention.

As shown in FIG. 2, the flow chamber 10 includes an inlet for receiving the particle containing fluid to be observed, and an outlet through which the fluid passes out of the flow chamber 10 after imaging and particle optical measurement functions have been performed. The flow chamber 10 is a low fluorescence structure of known dimensions and of an index of refraction of approximately 1.5. That is, it is fabricated of a material that does not readily fluoresce such as, for example, but without being limiting, microscope glass or rectangular glass extrusions. The flow chamber 10 is of rectangular shape and defines a channel 35 through which the fluid flows at a predetermined controllable rate. In some embodiments, the channel 35 within the flow chamber 10 is of rectangular configuration with a known cross sectional depth (D) and width (W). Light 32 which is glancing off inner wall 40 of the chamber 10 and light 34 which is reflecting off outer wall 41 of the chamber 10 represented in FIG. 2 are computer model generated depictions of reflections that occur in the chamber 10, wherein the lengths of light reflections represented by reflected arrows 37 and 38 indicate the amount of reflection occurring at different angles. The reflections are greatest at higher angles of incidence. In the case in which the fluid within the chamber 10 is water, at the water/inner wall 40 interface, the light 38 has its highest value at glancing angles near 90 degrees, or parallel to the surface at inner wall 40. This means that for best internal reflection within the chamber 10, the chamber 10 W/D ratio must be greater than 10:1 to allow the light 38 which is glancing off of the inner wall 40 of the chamber 25 and the light 37 which is reflecting off of the outer wall 41 of the chamber 10 to reflect at angles greater than 90 degrees and 50 degrees, respectively. The width of edge 50 of the chamber 10 is smaller than the field of view of the fluorescence analysis optics 16. An example of a suitable form of the flow chamber 10 and the field of view of the fluorescence analysis optics 16 is an RT5010 Vitrotube from Vitrocom, Inc. (River Lakes, N.J., US) which is matched with a fluorescence emission objective field of view of 300 micrometers. Inlet 52 of the flow chamber 10 is connectable to a fluid source such as sample source 54 and outlet 56 is connectable to a downstream device for transferring the fluid away from within the flow chamber 10 at a well-controlled, steady and adjustable rate. A suitable example of such a fluid transfer device is the pump 27, which may be a model 210 programmable syringe pump from KD Scientific, Inc. (Holliston, Mass., US).

The laser 12 is used to generate fluorescence and scatter light directed to the flow chamber 10, resulting in particle fluorescence and/or light scatter. The laser 12 may be a laser with an excitation filter 60. The laser 12 may be, but is not limited to, a 473 nanometer (nm), 488 nm or 532 nm solid state model laser available from an array of manufacturers known to those of skill in the art. Any particle fluorescence emissions from the flow chamber 12 that have a wavelength of 535 to 900 nm are detected by the fluorescence analysis optics 16, which includes at least the one or more emission filters 18, 19 and the one or more high sensitivity photomultiplier tubes (PMTs) 20,21. The emission filters 18, 19 should at least have the characteristic of being transparent to the fluorescence emissions of a desired fluorophore. An example of a suitable form of an emission filter 18, 19 is a 570/40 phycoerithryn emission filter available from Chroma Technologies (Rockingham, Vt., US); those of skill in the art will recognize that other suitable filters may be employed for the emission filters 18, 19. The PMTs 20, 21 should at least have the characteristic of being sensitive to the fluorescence emissions desired. An example of a suitable PMT is the H9656-20 model available from Hamamatsu (Bridgewater, N.J., US); those of skill in the art will recognize that other equivalent PMTs may be employed for the PMTs 20, 21.

Figure 3:
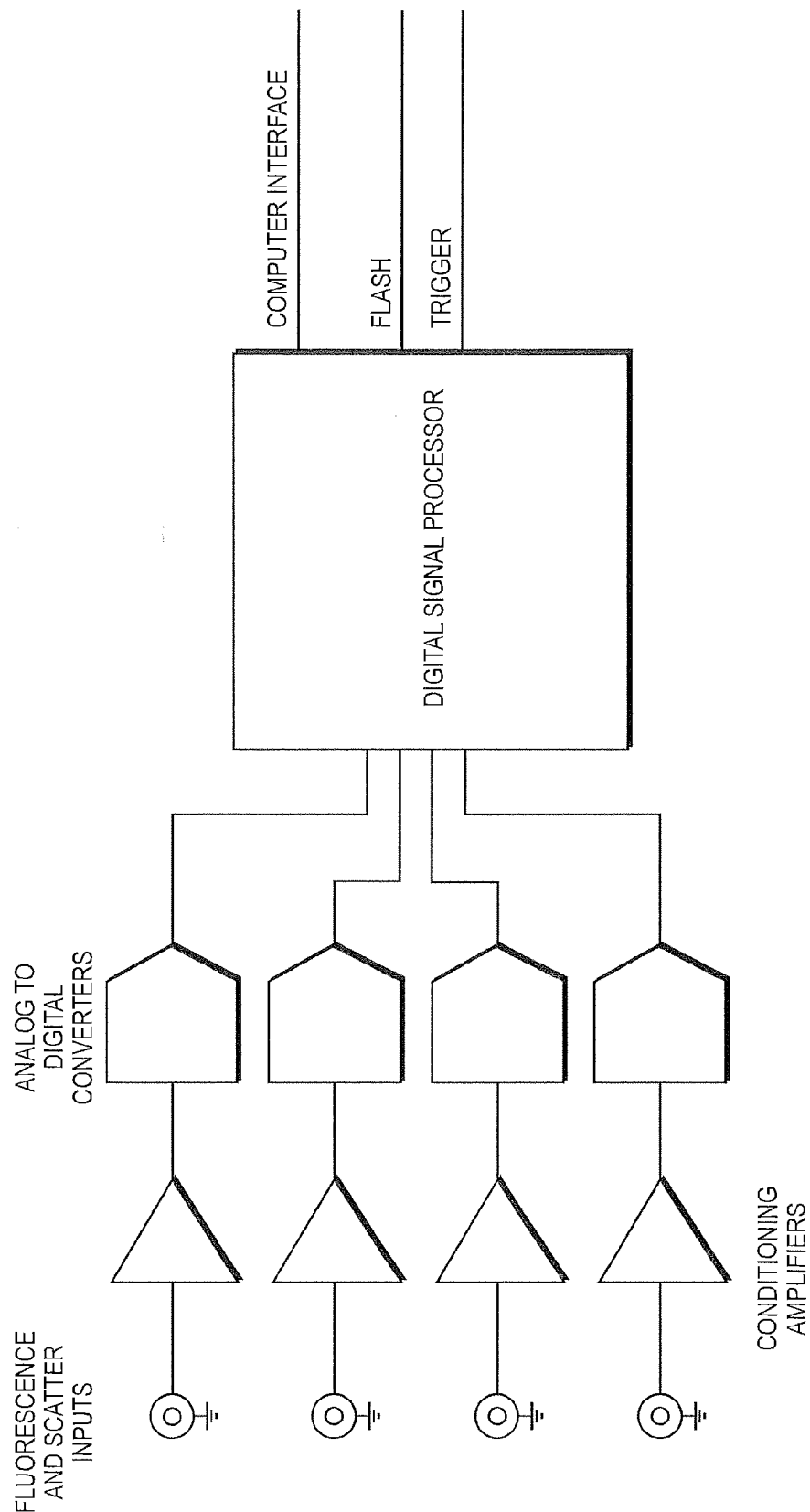
FIG. 3. is a diagram of the signal processor used in one embodiment of the invention.

Preferably, the signal processor 25 includes a user-adjusted threshold setting which determines the amount of fluorescence or scatter required for the present system to acknowledge a passing particle. For example, and in no means limiting the scope of the invention, the user may set the threshold to be 200 (dimensionless cytometer fluorescence or scatter units). One embodiment of a signal processor 25 that can be used in the system and method of the present invention is shown in FIG. 3. Scatter and fluorescence inputs are processed by conditioning amplifiers where they may be amplified and/or converted to their logarithm for better dynamic range as is commonly done in flow cytometers. These signals are then converted to digital signals which are analyzed by the signal processor 25. Programming of the signal processor 25 determines how it analyzes and reacts to these inputs.

When an input is greater than a predetermined threshold, indicating presence of a particle to be imaged, for example, the signal processor 25 initiates a camera trigger and then a flash signal to the backlighting source 22. The exposure of the camera and resultant imaging overlap the period where the sample is illuminated by the flash.

In the fluorescence and scatter mode of operation, when a fluorescent or light scattering particle passes through the area illuminated by the light source, the particle generates a signal which the signal processor 25 monitors. The signal processor 25 carries out an analysis interval to determine if the signal is strong enough to track, i.e., above the predetermined threshold. If the signal is strong enough as determined during the analysis interval, the signal processor 25 initiates a camera trigger pulse and then a flash signal to the backlighting source 22. The computing device 26 then reads in the resulting image and data regarding the scatter and/or fluorescence data. The computing device 26 is programmed to store the information received from the signal processor 25 and to make calculations associated with the particles detected. For example, but not limited thereto, the computing device 26 may be programmed to provide specific information regarding the fluorescence of the detected particles, the shape of the particles, dimensions of the particles, and specific features of the particles. The computing device 26 may be any sort of computing system suitable for receiving information, running software on its one or more processors, and producing output of information, including, but not limited to, images and data that may be observed on a user interface. An example of a suitable computing device at the time of the writing of this application is almost any personal computer.

The signal processor 25 is connected to the backlighting source 22 which, specifically, may be a light emitting diode (LED) or other suitable light generating means that produces a light of sufficient intensity to backlight the flow chamber 10 and image the passing particles. In one embodiment, the backlighting source 22 may be a very high intensity LED flash such as a 670 nm LED flash, or a flash of another suitable wavelength, which is flashed on one side of the flow chamber 10 for 200 μsec (or less). At the same time, the image capturing system 24 positioned on the opposing side of the flow chamber 10 is activated to capture an instantaneous image of the particles in the fluid as "frozen" when the high intensity flash occurs. The image capturing system 24 is arranged to either retain the captured image, transfer it to the computing device 26, or a combination of the two. The image capturing system 24 includes characteristics of a digital camera or an analog camera with a framegrabber or other means for retaining images. For example, but in no way limiting what this particular component of the system may be, the image capturing system 24 may be a CCD firewire, a CCD USB-based camera, a CMOS camera, or other suitable device that can be used to capture images and that further preferably includes intrinsic computing means or that may be coupled to computing device 26 for the purpose of retaining images and to manipulate those images as desired. The computing device 26 may be programmed to measure the size and shape of the particle captured by the image capturing system 24 and/or to store the data for later analysis.

Figure 4:
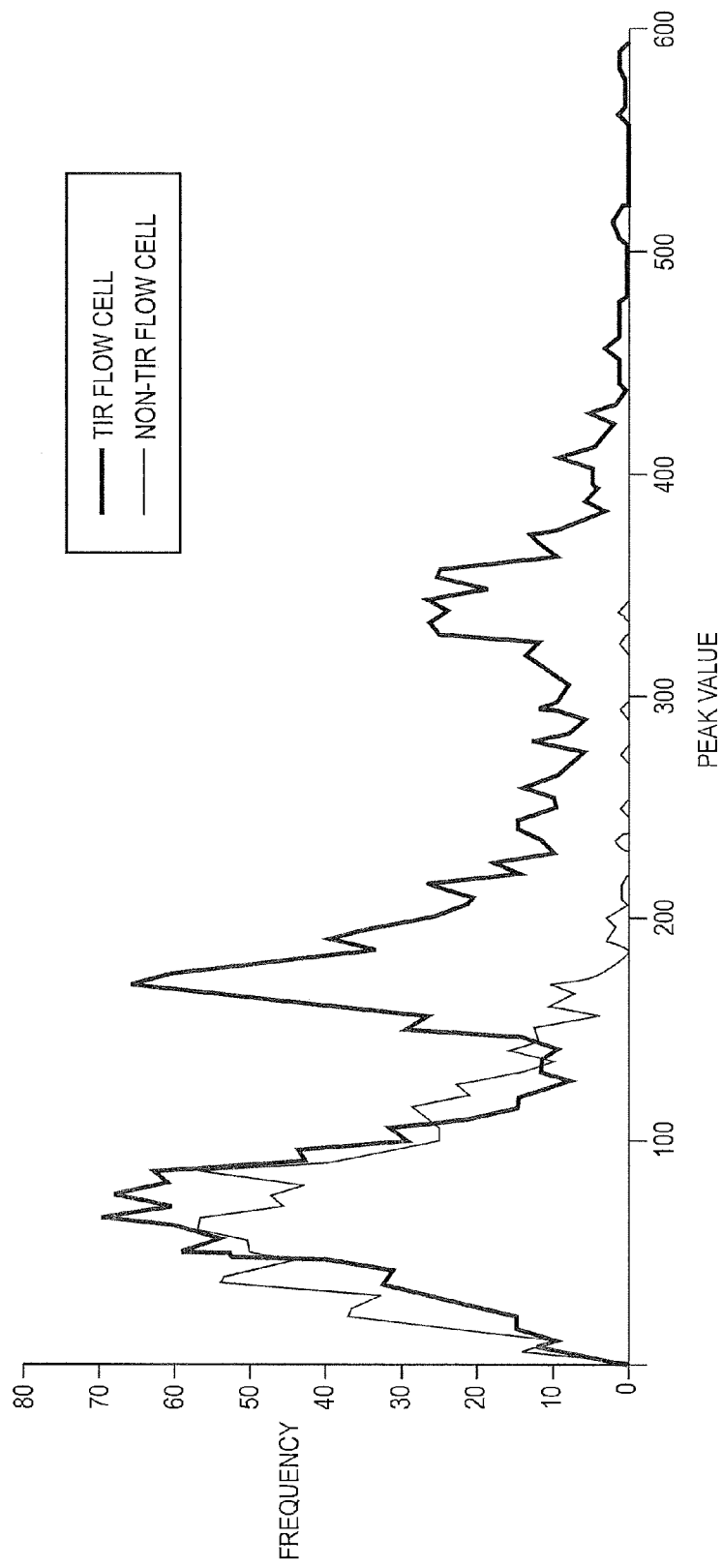
FIG. 4. is a plot of fluorescence standard peak histograms taken with a non-TIR flow cell and a TIR-capable flow cell.
Figure 5:
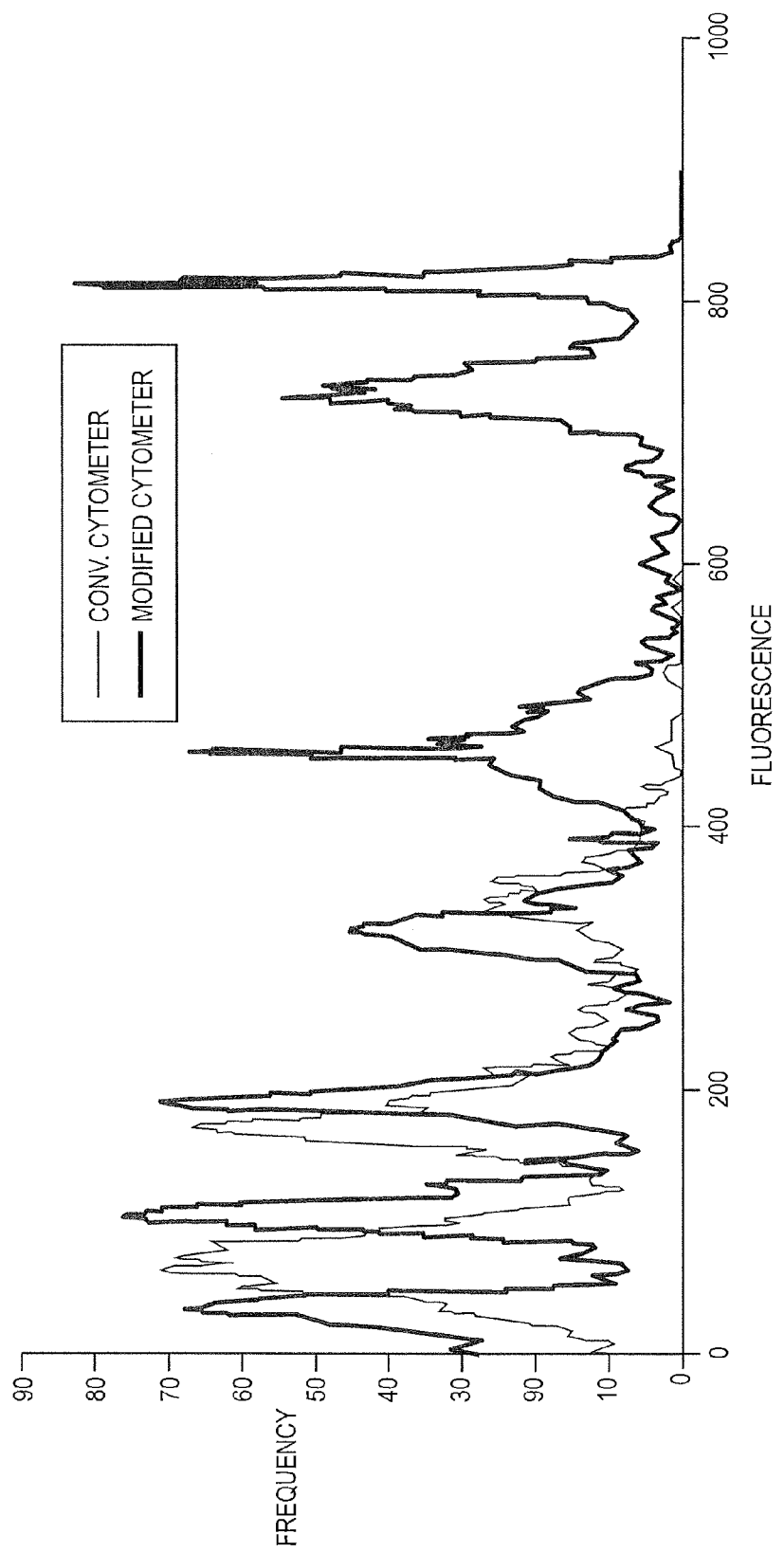
FIG. 5. is a plot of maximum sensitivity performance peak histograms taken with a conventional imaging flow cytometer and with a system modified to use a TIR-capable flow cell.

The advantages associated with the total internal reflection enhanced imaging flow cytometer system and related method of detecting particles in a fluid of the present invention may be readily observed by viewing FIGS. 4 and 5. FIG. 4 displays the measured distribution of fluorescence values of a fluorescent particle standard containing 3 micrometer polystyrene beads with eight different possible fluorescence peak values. These peaks are spaced in intensity at about 2.6 per decade of intensity. These were measured with an imaging flow cytometer of the present invention using a total internal reflection (TIR)-enhanced flow cell and a non-TIR enhanced flow cell with dimensions too large to allow internal reflections. The TIR-enhanced flow cell allowed the measurement of three of these peaks whereas, using the same cytometer, the non-TIR enhanced flow cell allowed the measurement of one peak, meaning that the TIR-enhanced flow cell of the present invention made the cytometer almost 10 times more sensitive to the beads with all else being equal.

FIG. 5 displays the measured distribution of fluorescence values of the same fluorescence standard when analyzed with a commercially available imaging flow cytometer, the one described in U.S. Pat. No. 6,115,118 and that same cytometer configuration modified to accommodate the TIR-capable flow cell of the present invention. Due to the much lower autofluorescence of the fluorescence analysis optics, the modified TIR-capable cytometer system was modified with a much more powerful laser and as such was much more sensitive to fluorescing particles. It was possible to convert a cytometer which could measure three peaks to a system which could measure seven peaks; an increase in sensitivity of 800.

Figure 6:
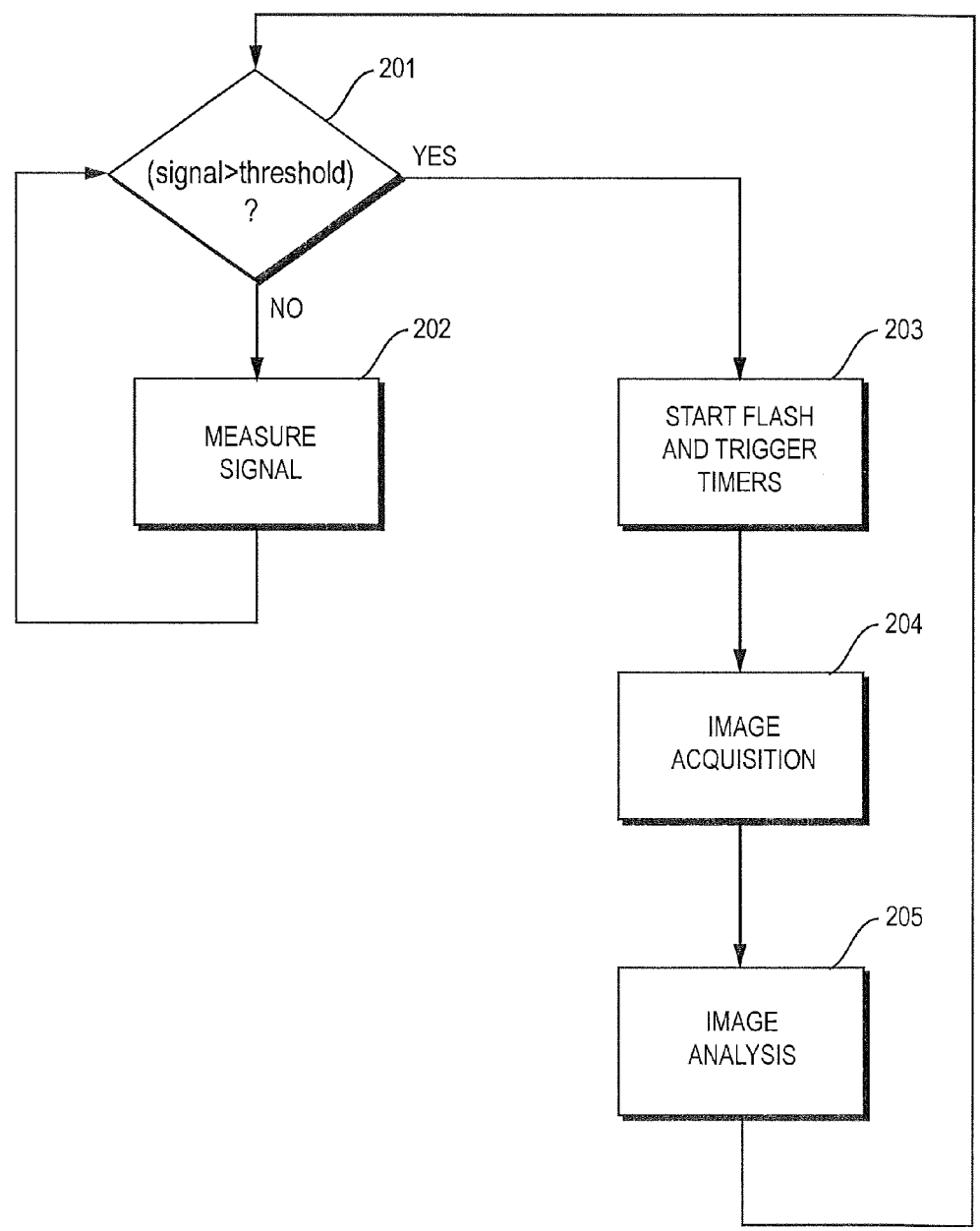
FIG. 6. is a diagram representing the steps of the method of particle detection of the present invention.

As represented in FIG. 6, a method 200 of the present invention includes steps associated with capturing images with the system of the present invention. Several processes occur on a continuous basis during normal operation. For example, in one embodiment, the pump 27 draws the sample through the flow chamber 10 at a constant rate. The flow chamber 10 is illuminated with excitation light from the laser 12 continuously. The fluorescence analysis optics 16 provide fluorescence analog waveforms to the inputs of the signal processor 25. Finally, the signal processor 25 continuously reads these signals.

In addition to these continuous processes, discrete steps are carried out. During step 201, fluorescence signals from the PMTs 20, 21, are compared to a preset threshold. If the signals are not greater than the threshold, the waveforms are measured again in step 202. If they are greater than the threshold, the digital signal processor 25 executes step 203, where the signal processor 25 activates the image capturing system and flash so that the system can capture an image of the passing particle while the high intensity flash occurs. During step 204 of the method of the present invention, the image capturing system 24 transfers the captured image to the computing device 26. During the image analysis step 205, the computing device analyzes the image for particles and if any particles with acceptable characteristics are found, the device stores their images and their fluorescence, scatter and other measurements.

The present invention has been described with respect to a particular embodiment. Nevertheless, it is to be understood that various modifications may be made without departing from the spirit and scope of the invention. All equivalents are deemed to fall within the scope of this description of the invention.

What is claimed is:

1. A system for imaging particles in a fluid, the system comprising:
   a. A rectangular flow chamber having a width dimension and a depth dimension, the flow chamber including a channel arranged to transport the fluid therethrough at a selectable rate, wherein the flow chamber is a low fluorescence structure with an index of refraction of about 1.5 and having a ratio of the width dimension to the depth dimension that is greater than 10:1;
   b. a device configured to create a controllable fluid flow rate in the flow chamber;
   c. a backlighting generator arranged to illuminate the fluid in the flow chamber;
   d. an objective arranged to receive incident optical radiation from the flow chamber;
   e. a light source arranged to generate light scatter and/or fluorescence from particles;
   f. one or more detectors to detect light scatter and/or fluorescence emitted from the particles upon illumination;
   g. a signal processor configured to receive signals from the one or more detectors; and
   h. an image capturing system including means to capture images of particles in the fluid.

2. The system of claim 1, wherein the backlighting generator is a light emitting diode flash.

3. The system of claim 1, wherein the backlighting generator generates a high intensity flash.

4. The system of claim 1, wherein the system further includes a computing device to receive signals from the image capturing system.

5. The system of claim 1, wherein the image capturing system includes a computing device.

6. The system of claim 1, wherein the image capturing system includes a digital camera or an analog camera and a framegrabber.

7. The system of claim 1, wherein the image capturing system includes a CCD or a CMOS camera.

8. The system of claim 1, wherein the light source is a laser.

9. An apparatus to assist in the imaging of particles in a fluid, the apparatus comprising a rectangular flow chamber having a width dimension and a depth dimension and including a channel arranged to transport the fluid therethrough at a selectable rate, wherein the flow chamber is configured with a ratio of the width dimension to the depth dimension that is greater than 10:1 to enable fluorescence propagation from the fluid within the channel to an edge of the flow chamber for enhanced light collection of the fluorescence.

10. A method for imaging particles in a fluid which is transported through a channel of a rectangular flow chamber at a selectable rate and illuminated with a light source so that scatter and/or fluorescence signals are detected, the method comprising the steps of:
   a. directing the fluid through the flow chamber, wherein the flow chamber is configured with a ratio of the width dimension to the depth dimension that is greater than 10:1 to enable fluorescence propagation from the fluid within the channel to an edge of the flow chamber for enhanced light collection of the fluorescence; and
   b. imaging the tracked particle and transferring the captured images to a computing device.

11. The method of claim 10, wherein the method further includes the step of analyzing the image for particles.

12. The method of claim 10, wherein the backlighting generator is a light emitting diode flash.

13. A method for imaging particles in a fluid, the method comprising the steps of:
   a. transporting the fluid through a channel of a rectangular flow chamber at a selectable rate, wherein the flow chamber is configured with a ratio of the width dimension to the depth dimension that is greater than 10:1 to enable fluorescence propagation from the fluid within the channel to an edge of the flow chamber for enhanced light collection of the fluorescence;
   b. illuminating the fluid with a light source arranged to generate light scatter and/or fluorescence from the particles;
   c. transmitting a signal from a scatter detector and/or a fluorescence detector to a signal processor and, if the signal meets a predetermined threshold, initiating a particle tracking interval including controlling a tracking mirror, activating a backlighting generator, and activating an image capturing system; and
   d. imaging the tracked particle and transferring the captured images to a computing device.

14. The method of claim 13, wherein the method further includes the step of analyzing the image for particles.

15. The method of claim 13, wherein the backlighting generator is a light emitting diode flash.

* * * * *